(12) United States Patent
Houston et al.

(10) Patent No.: US 7,682,673 B2
(45) Date of Patent: *Mar. 23, 2010

(54) BLOOD-FLOW TUBING

(75) Inventors: John Graeme Houston, Tayside (GB); John Bruce Cameron Dick, Tayside (GB); Peter Stonebridge, Tayside (GB)

(73) Assignee: Tayside Flow Technologies Limited, Dundee (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/650,217

(22) Filed: Aug. 19, 2003

(65) Prior Publication Data

US 2004/0037986 A1  Feb. 26, 2004

Related U.S. Application Data

(63) Continuation of application No. 09/869,661, filed on Jun. 29, 2001, now abandoned, application No. PCT/GB99/04449, filed on Dec. 23, 1999.

(30) Foreign Application Priority Data

Dec. 28, 1998 (GB) ................... 9828696.6

(51) Int. Cl.
*A61F 2/82* (2006.01)
*B32B 1/08* (2006.01)

(52) U.S. Cl. ............ 428/35.8; 623/1.1; 623/1.15; 623/1.22; 428/36.1; 428/36.9

(58) Field of Classification Search ........... 428/34.1, 428/35.7, 35.8, 36.9, 36.1; 604/4.01, 5.01, 604/6.1, 93.01; 623/1.1, 1.15, 1.2, 1.24, 623/1.35, 1.12, 1.13, 1.32, 1.33; 138/118, 138/121, 122
See application file for complete search history.

(56) References Cited

U.S. PATENT DOCUMENTS

| | | | |
|---|---|---|---|
| 4,596,548 A | | 6/1986 | DeVries et al. |
| 4,629,458 A | | 12/1986 | Pinchuk |
| 5,653,745 A | * | 8/1997 | Trescony et al. ........... 623/1.29 |
| 5,989,230 A | * | 11/1999 | Frassica ..................... 604/264 |
| 6,500,186 B2 | * | 12/2002 | Lafontaine et al. .......... 606/159 |
| 7,185,677 B2 | * | 3/2007 | Houston et al. ............... 138/39 |
| 7,331,989 B2 | * | 2/2008 | Houston et al. ............ 623/1.22 |
| 2003/0225453 A1 | | 12/2003 | Murch |

FOREIGN PATENT DOCUMENTS

| | | |
|---|---|---|
| EP | 0612536 | 8/1994 |
| FR | 2657945 | 8/1991 |

(Continued)

OTHER PUBLICATIONS

Foreign priority document: GB 9828696.6, filed Dec. 28, 1998.*

(Continued)

*Primary Examiner*—Rena L Dye
*Assistant Examiner*—Walter B Aughenbaugh
(74) *Attorney, Agent, or Firm*—Bracewell & Giuliani LLP

(57) ABSTRACT

An artificial or modified natural blood flow tubing has a helical-flow inducer to induce helical flow in such fashion as to eliminate or reduce turbulence. One inducer is a tubular stent of expansible mesh having a helical vane.

9 Claims, 3 Drawing Sheets

| | FOREIGN PATENT DOCUMENTS | |
|---|---|---|
| GB | 2092894 | 8/1982 |
| WO | WO 93/15661 | 8/1993 |
| WO | WO 95/20986 | 8/1995 |
| WO | WO95/35072 | 12/1995 |
| WO | WO98/26731 | 6/1998 |
| WO | WO 98/53764 | 12/1998 |
| WO | 0189419 A1 | 11/2001 |

OTHER PUBLICATIONS

P.A. Stonebridge; Spiral laminar flow in vivo; Journal; Sep. 22, 1995; 5 Pages; Clinical Science; Edinburgh, U.K.

P.A. Stonebridge; Spiral laminar flow in arteries?; Journal; Nov. 30, 1991; 2 Pages; vol. 338; The Lancet.

* cited by examiner

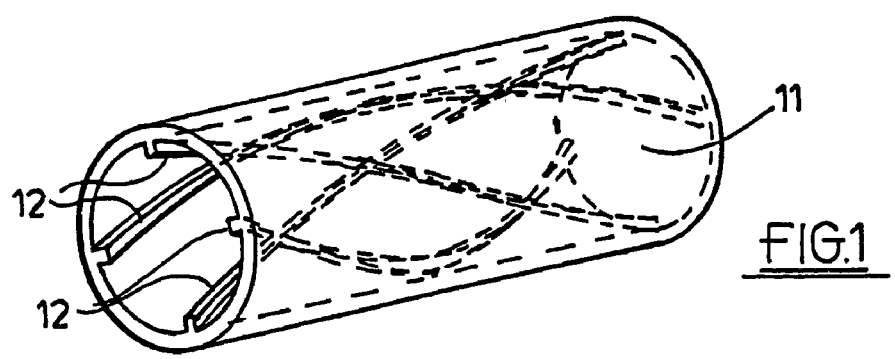
FIG. 1
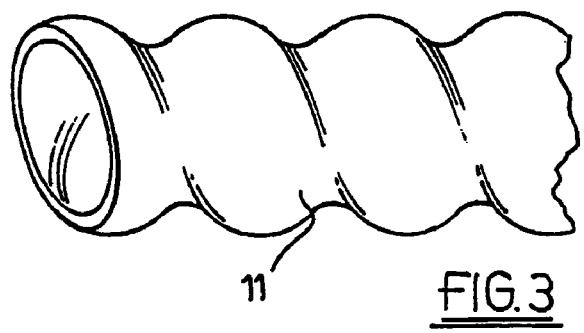
FIG. 3
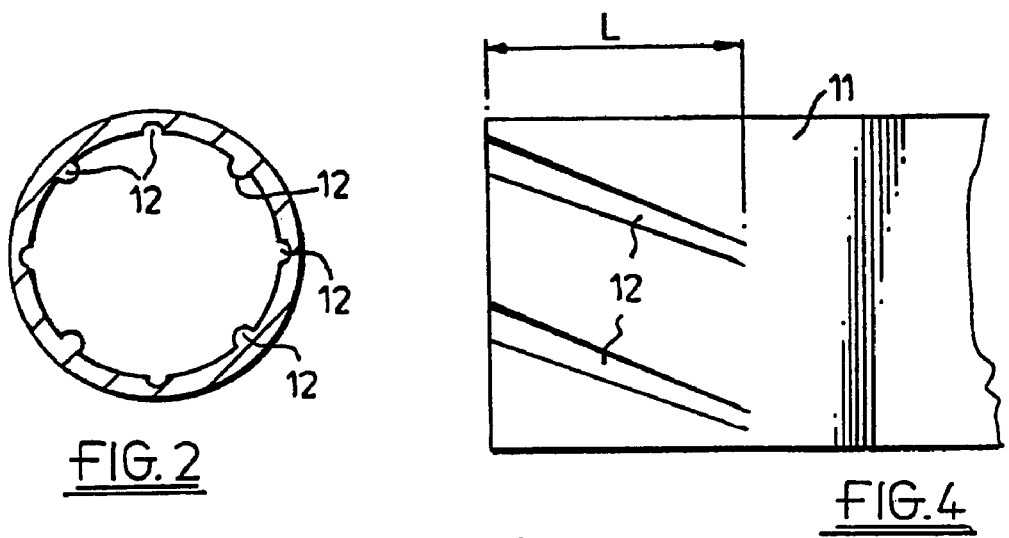
FIG. 2
FIG. 4
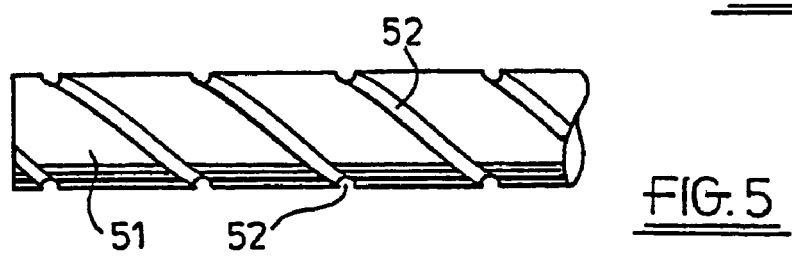
FIG. 5

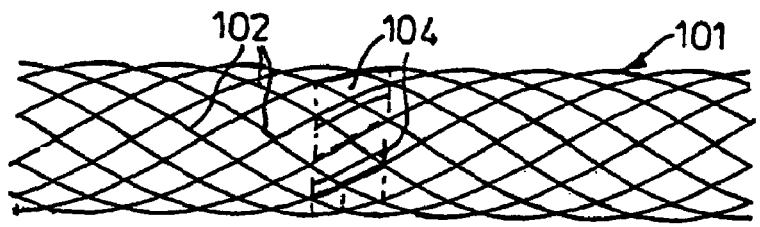
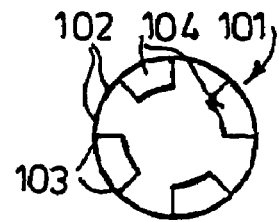
FIG. 9
FIG. 10
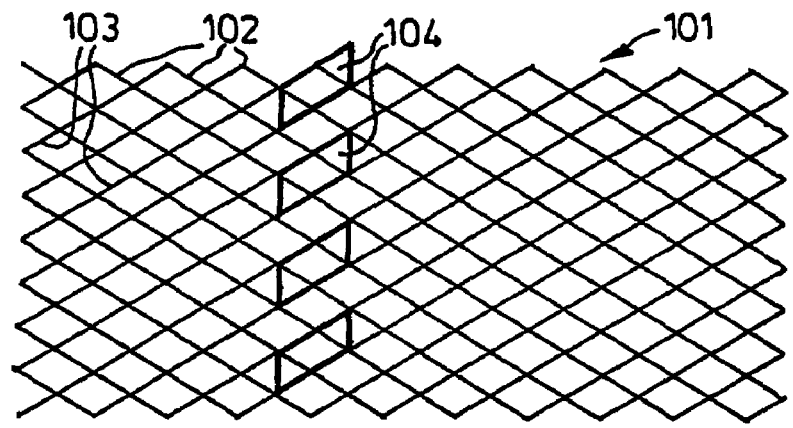
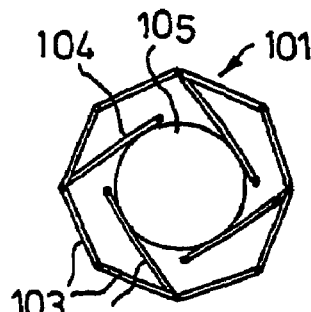
FIG. 11
FIG. 12
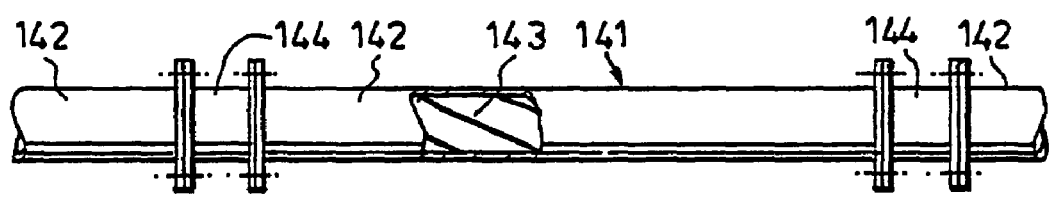
FIG. 13
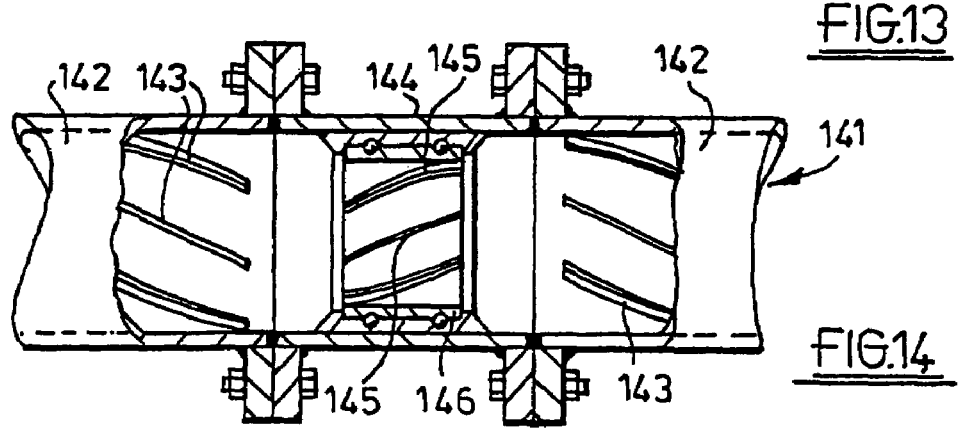
FIG. 14

BLOOD-FLOW TUBING

This application is a continuation of application Ser. No. 09/869,661, filed Jun. 29, 2001, now abandoned which claimed priority from PCT No. PCT/GB99/04449, filed Dec. 23, 1999 which claimed priority from U.K. application Serial No. 9828686.6, filed Dec. 28, 1998.

BACKGROUND

1. Field of the Invention

This invention relates inter alia to artificial or modified natural blood-flow tubing, by which is meant artificial vascular prostheses or modified natural grafts or autografts, and tubing in which blood flows outside the body, e.g. in dialysis or in open heart surgery. Indeed, the invention might well extend to any tubing that carries a laminar flow, and particularly, but by no means exclusively, a pulsatile flow.

2. Description of the Related Art

Spiral flow has been observed (Stonebridge P. A. and Brophy C. M., 1991, Spiral laminar flow in arteries? Lancet 338: 1360-61) during angioscopy, as has the presence of spiral folds on the endoluminal surface of blood-vessels. The observation, it was said could have been an artifact of angioscopy, or the phenomenon may occur only in diseased arteries because of turbulence generated atherosclerosis, or it may be physiological, the latter having some support from other observations of rotational flow.

Indeed, in this seminal article, it is remarked that, if confirmed, the existence of spiral rather than laminar blood flow in peripheral arteries would have striking implications for the understanding of haemodynamics, arterial wall function, the pathogenesis of atherosclerosis and intimal hyperplasia, and the design of prosthetic graft materials.

Confirmation came with the publication by Stonebridge and others of a paper "Spiral laminar flow in vivo" in Clinical Science (1996, 9: 17-21) in which, using standard color flow Döppler techniques, velocity information was obtained, from which a rotational element to forward flow during all or part of the pulse cycle was demonstrated in each of eleven healthy male volunteers.

However, even with this confirmation, it was admitted that it had not yet been shown whether angioscopic observations of a spiral pattern on the endoluminal surface of arteries and spiral flow patterns were real events or observational artefacts.

More recent work with magnetic resonance imaging ("MRI") has established, however, that rotational flow is beneficial at least in certain situations and is presumed, on that account, to be "selected for".

The prediction, therefore, by Stonebridge and Brophy in the 1991 Lancet report is vindicated, though it has only now become apparent just how to design prosthetic graft materials in order to reproduce, or at least not to destroy, the physiological rotation, and not at the same time bring about any disadvantages. It has also become apparent that the findings are of interest in connection with blood flow tubing other than grafts, and, indeed, with other tubing as well.

BRIEF SUMMARY OF THE INVENTION

The invention comprises, in one aspect, tubing, especially, but not exclusively artificial or modified natural blood flow tubing, having helical-flow inducing means adapted to induce helical flow in such fashion as to eliminate or reduce turbulence.

The tubing may have internal helical grooving and/or ridging, which may be multi-start grooving and/or ridging. The grooves and ridges may be of any cross-sectional shape and size, for example semicircular, square, triangular or sinusoidal—some may be found more effective than others in particular circumstances.

By "helical" as used herein is meant "generally helical", rather than necessarily always mathematically precisely helical.

Instead of, or in addition to grooving and/or ridging, the tubing may be of non-circular cross-section, twisted. Synthetic or other thermoplastic or plastifiable and re-settable material made as a straight, circular or non-circular cross-section tube, may be plastified and reset in twisted or corkscrew condition. Non-circular can, of course, include, elliptical, semi-circular, triangular, square or any other convenient or appropriate shape, including shapes with wavy peripheries which, when twisted, will form grooves and/or ridges.

The helical formation may have a constant helix angle along at least a part of its length, or one which reduces or increases over at least part of its length The grooving and/or ridging, where present, may taper in the direction of flow or in the opposite direction.

The helical formation may have a helix angle between 5° and 50°, for example, about 16°. A helical formation having an increasing or reducing helix angle over at least a part of its length may have an angle of 16°, for example, at the start or the finish of the taper, or somewhere in between. Angles outwith the suggested range may be found useful, but it is thought the angles above 50° will unduly restrict flow, whereas angles much below 5° will be significantly less effective that those in the range. The optimal helix angle will be determined by factors such as the diameter, longitudinal velocity and rotational velocity. In turn, these factors are determined by the particular clinical problem, eg. the type of vessel, the patient's age and the size of the native vessel.

The helical flow inducing means may comprise a biocompatible insert, which may comprise helical vane means, which may, for example, be fashioned like fan or propeller blades or which might be elongated spiral projections from the inner surface of a cylindrical insert.

The tubing may have a branched structure in which the flow is from a first branch into two second branches in which helical-flow inducing means are provided where the tubing branches so as to eliminate or reduce turbulence downstream from the first branch. The same may be provided for confluent branches, of course.

The invention also comprises a method for making blood flow tubing comprising forming the tubing on a mandrel which has helical grooving and/or ridging at least over part of its length. The tubing may be formed, for example, by coagulation casting. In another method, tubing may be formed as cylindrical tubing and a helical formation imparted thereto by wrapping with a thread; the tubing and/or the thread may comprise thermoplastic material, and the tube heat set to remain stable in the helical formation. In yet other methods, tubing may be formed by woven or knitted graft, or extrusion.

In yet another method, a non-circular section tube may be formed with a twisted cross-section either directly on a mandrel itself having a twisted non-circular cross-section or by making a tube with non-circular, non-twisted cross-section and then twisting, plastifying and re-setting the tube in the twisted configuration.

Tubing made as described may be adapted for use as a vascular prosthesis for implanting into the human or animal body. After-care may involve confirming the helical-flow inducing effect of implanted tubing by measurement of a rotational component of flow, e.g. by MRI, or Döppler ultrasound.

A method for use in designing tubing for implant in various locations in the cardio-vascular system may, according to the invention, involve taking measurements of rotational flow in such locations, as by MRI, in a healthy population in order to determine a typical healthy flow, and designing tubing adapted to produce such flow in such locations. Additionally, a method for use in selecting tubing for implant in various locations of a cardio-vascular system of a specific patient may involve taking measurements of rotational flow in such locations in said patient in order to determine flow, and selecting tubing to produce such flow in such locations (a pre-intervention method, which may be facilitated by computer software to aid selection). The design may be by mathematical modelling or by trial and error (ex vivo, preferably), with, perhaps, "fine tuning" by after-care measurement comparing predicted with actual flows to improve subsequent prostheses.

Also, according to the invention, intravascular stents, for insertion e.g. during angioplasty procedures, can have spiral-flow inducing properties.

The present invention may also be utilized for stent grafts, ie. a combination of stent (providing structure) and graft (internal or external material covering).

A stent, for example, of an expansible mesh material, which is inserted by catheterisation in collapsed form and which becomes expanded on release from the catheter, may have an internal spiral formation after expansion. Stent which are currently used include those which are self-expanding on release from the catheter, and those which are induced to expand by mechanical means, eg. using a balloon. The mesh material may comprise segments extending helically around the periphery of the stent and the internal spiral formation comprise vane members attached to such segments—in other words, the design parameters for the stent may include both internal and external modification. Styles of stent may be, for example, mesh (made of configuration of strands or wires giving structure), expanded sheet (made, cut and modified from sheet) and wire spring.

Where an insert is used which is accessible, e.g. during vascular imaging, it may be made adjustable, for example its helix angle may be increased or decreased by extending or contacting a flexible vane arrangement on a rigid support, and this may be done during angioscopy with simultaneous measurement of the rotational component of flow produced by the insert, whereby to achieve a desired flow.

Tubing according to the invention may, however, be adapted for use in or with blood treatment or delivery equipment, such as a heart-lung machine, dialysis equipment or a giving set.

More generally, the invention comprises tubing having helical-flow inducing means adapted to induce helical flow in such fashion as to eliminate or reduce turbulence or dead flow regions, regardless of the use to which such tubing as adapted.

Tubing may be utilized to optimize mixing and exhaust of fluid. For example, the tubing design may encourage mixing so as to reduce sedimentation, or may beneficially affect the fluid flow pattern (eg. spiral) beyond the outlet of the tubing. The latter effect may be applied, for example, in tubing such as hoses and firehoses. Optimisation of tubing characteristics may result in a reduction of fluid noise at the exhaust or vibration in the tubing.

The term "tubing" as used here may include all types of conduit which transport or contain liquid or gaseous fluid, in both blood and non-blood fields. Tubing for the blood field may include, but is not restricted to, graft stems and giving sets.

Such tubing may have, as with blood flow tubing, internal helical ridging and/or grooving, and other attributes of the blood flow tubing above referred to. It may particularly be used in plant for delivering slurries or suspensions of solids in liquids, or, for example, as pipeline for delivering viscous liquids such as oils. It may have helical flow inducing means at least at interfaces with supply or storage vessels, and at branches.

The helical flow inducing means may comprise active flow rotating means, such for example as driven vanes, and such active flow rotating means may be situated at intervals, for example, along a pipeline.

BRIEF DESCRIPTION OF THE DRAWINGS

Embodiments of tubing and methods of making and using the same in accordance with the invention will now be described with reference to the accompanying drawings, in which:

FIG. 1 is a perspective view of a short length of tubing of a first embodiment suitable for prosthetic implant in a cardio-vascular system;

FIG. 2 is a cross-section of a second embodiment of tubing;

FIG. 3 is a perspective view of a third embodiment;

FIG. 4 is a view of the inside of a length of tubing, opened out;

FIG. 5 in an elevation of a mandrel for use in casting tubing according to the invention;

FIG. 9 is a view of a mesh material stent from the side, in its expanded condition;

FIG. 10 is an end-on view of the stent of FIG. 9;

FIG. 11 is an opened-out view of the stent of FIG. 10;

FIG. 12 is an end-on view, to a larger scale, of the stent of FIG. 11 in its collapsed condition, before release from the catheter;

FIG. 13 is a view of a pipeline, with active helical-flow inducing means; and

FIG. 14 is a section through the pipeline of FIG. 13.

DETAILED DESCRIPTION OF THE INVENTION

Figure 6:
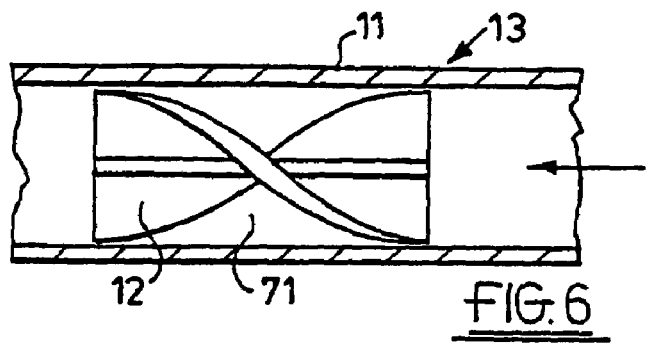
FIG. 6 is a view of a vaned device in a tube.

The drawings illustrate blood-flow tubing 11 having helical-flow inducing means 12 adapted to induce helical flow in such fashion as to eliminate or reduce turbulence. The tubing may be artificial, for example woven or knitted synthetic polymer fibre, in which the helical-flow inducing means may be knitted or woven structure as by three dimensional knitted or woven formation, or extruded or cast tubing, or modified natural, e. g. autograft material with an insert or with grooving made e. g. by a laser.

The helical-flow inducing means 12 may comprise grooving 14 and/or ridging 15, which may be multi-start grooving and/or ridging as seen in FIGS. 1, 2 and 4. Square-section ridging, as seen in FIG. 1, or grooving, or semi-circular section ridging and/or grooving, as seen in FIG. 2, can be used, but other cross-sections will serve as well, for example, triangular.

However, as seen in FIG. 3, a non-circular section tube 11 can have a twist, and may also have internal ridging and/or grooving. A twisted tube may be cast as such on a twisted mandrel or, if, for example, of thermoplastic material, may be twisted and heat-set in that state. Even a circular-section tube, bent into a corkscrew shape, can, if the dimensions are appropriate for the density, velocity and viscosity of the liquid flowing through it, give rise to a circulation in the flow.

The helical-flow inducing means may extend over the whole length of the tubing. It seems, on present knowledge, to be important at least to provide it where turbulence is likely to occur, for example at the inlet or outlet from the tubing, or in branched tubing as seen in FIG. 9, where turbulence can be occasioned in the branch region and can be controlled by ridging and/or grooving 12 at the inlets to the two minor branches 11b where they join the main branch 11a, and/or in the main branch 11a itself. It may be found desirable to have different ridging and/or grooving in the two minor branches, where, for example, they run at different angles to the main branch.

It may be arranged that the ridging and/or grooving 12 has a reducing helix angle in the flow direction over at least part of its length—this is illustrated in FIG. 4, where the grooving 12 is also tapered so as to extend only over an inlet region L, but the tapering and reducing angle could extend over longer lengths of tubing. The opposite—helix angle increasing and/or depth of grooving or height of ridging increasing in the flow direction may also be appropriate in some circumstances.

The appropriate helix angle, or range of helix angles, where increasing or decreasing angles are used, will depend on a number of factors, principally, the dimensions of the tubing, the density and viscosity of the liquid flowing through it, and the velocity of the liquid flow. Generally, it is supposed that angles between 5° and 50°, preferably about 16° will give best results, but angles outside this range may also be found to be useful in some circumstances.

FIG. 5 is an elevation of a mandrel 51 such as may be used in a coagulation casting process to make prosthesis of polyetherurethane or other biocompatible polymer. Grooves 52 are provided on the mandrel 51 which then forms a tube with internal ridging.

Figure 7:
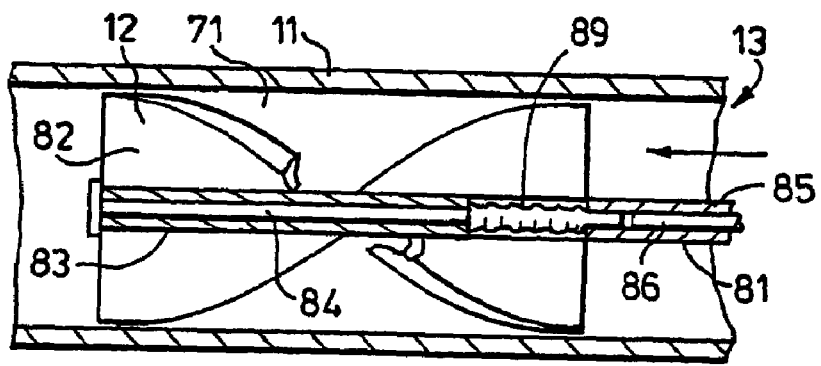
FIG. 7 is a view of a second vaned device in a tube.
Figure 8:
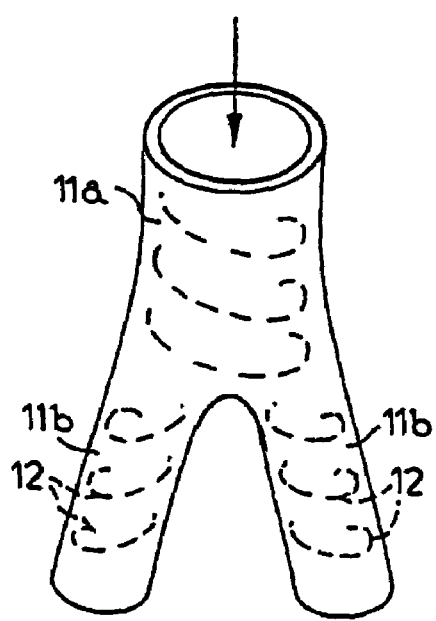
FIG. 8 is a view of a branched tube according to the invention.

FIGS. 6 and 7 illustrate helical vane devices 71 which can be inserted in tubing to cause helical flow. In FIG. 7 the effect can be increased by a probe 81 as used in angiography. The vanes 82 are on a sleeve 83 and sufficiently flexible to be compressed on a rigid support 84 by a sleeve 85 of the probe 81 being advanced relative to a core 86, the core 86 engaging the support 84 while the sleeve 85 is advanced against the sleeve 83, the sleeve 83 being held in the compressed state by a ratchet arrangement 89 between support 84 and sleeve 83. Such a device may be adjusted during angiography while observing the rotational flow induced, thereby, e.g. by MRI. The adjustment may be effected in any other fashion, e.g. by the application of torque to one end while holding the other end fixed.

FIGS. 9 to 12 illustrate an expansible mesh material stent 101 which is inserted by catheterisation. Such stents are sometimes made of a metal with a shape memory and are presented on a catheter in collapsed form, expanding on release from the catheter as they reach body temperature, others expand elastically as they are pushed from a captive surround. In its expanded condition, as shown in FIGS. 9 and 10, the stent 101 comprises a mesh cylinder formed, for example, of welded wires 102 with joined segments 103 extending helically around the periphery of the stent 101, though some stents are of expanded metal sheet, in which case the segments would be integral strips. Attached to some of the segments 102, on the inside of the stent 101, are vane members 104. In a welded wire construction, these could be plates welded to segments, while in an expanded sheet construction, the vane members 104 could be parts of the sheet, leaving corresponding holes in the mesh. FIG. 11 shows an opened-out version of the stent 101, as if cut along a generator of the cylinder and laid flat, with the inside face uppermost. FIG. 12, which is to a larger scale, shows the stent 101 in collapsed form around a catheter wire 105, without, however, the associated surround which contains them for insertion and out from which they are pushed once maneuvered into position.

Aside from blood flow tubing for implantation, or devices for use in improving circulation, such as bypasses and stents, blood flow tubing is found in various items of medical equipment such as heart-lung machines, dialysis machines and blood transfusion equipment. Inasmuch as, in such equipment, blood flows much as it does in the body, it could be at least as important to fashion such tubing to give the best possible flow characteristics, in particular, the avoidance of thromboses being generated during prolonged use of the equipment, as in heart surgery and dialysis, and the principles set out above in relation to natural and artificial grafts can also be applied to such external blood flow tubing. Even in giving sets, where flow rate is likely to be low, helical flow may well be found to have advantages, especially at the interfaces between tubing and cannulae and flow regulators.

FIGS. 13 and 14 illustrate, by way of example, the application of the notion of helical flow to an oil pipeline 141, The pipeline 141 is itself made up from pipe sections 142, which may themselves have internal helical grooving and/or ridging 143. In addition, active flow rotating means 144 are provided at intervals along the pipeline 141, at junctions between pipe sections 142. The active flow rotating means comprise, as seen in FIG. 13, rotary vanes 145 mounted in connecting rings 146. Depending on circumstances, it may be desirable to drive the vanes by external means, such, for example, as a motor, which can be, for example, solar powered, or it may be preferred to derive power for rotating the vanes from the flow itself, the general idea being to refresh any swirl component that might have attenuated over the preceding pipe section.

In addition to pipelines, the idea of helical flow will clearly be of benefit in plant in which slurries and suspensions of solids in liquids are transported between reactors and storage tanks, for instance. Examples of such plants are food producing plants, where soups, sauces and like products are manufactured.

It is noted that the mere provision of helical flow induction will not necessarily reduce or eliminate turbulence. It will be important to select the most appropriate configuration, which may well be done by trial and error. It may, of course, be found, especially where sharp bends or corners are encountered in the tubing, that there is a limit to the stability of rotational flow—it may be desirable, if possible, to refashion the tubing to eliminate sharp bends or corners before helical flow will have the effect of inducing or maintaining non-turbulent flow.

Designs for the tubing and methods for making the same other than those already discussed can of course be envisioned, all falling within the scope of the invention.

The invention claimed is:

1. An intravascular stent comprising a metal tubular mesh member, the tubular mesh member having an internal helical formation to induce spiral-flow therethrough, the internal helical formation having a helix angle between 5 and 16 degrees relative to a longitudinal axis of the stent.

2. The stent according to claim 1, wherein the tubular mesh member is expansible and is inserted by catheterization in collapsed form and which becomes expanded on release from the catheter, the internal helical formation being attached to an interior portion of the tubular mesh member.

3. The stent according to claim 2, wherein the tubular mesh member comprises crisscrossed wires extending helically around the periphery of the stent, and the internal helical formation comprises a helical vane member attached to such wires.

4. The intravascular stent according to claim 1, wherein the helix angle of the internal helical formation is adjustable.

5. The intravascular stent according to claim 1, wherein the internal helical formation comprises:
   a rigid support coaxially mounted within the tubular mesh member; and
   a spiral flow inducer vane surrounding and extending from the rigid support.

6. The stent according to claim 1, wherein the internal helical formation comprises:
   a rigid support rod coaxially mounted in the tubular member;
   a flexible sleeve within the tubular member and surrounding the support rod;
   a flexible helical vane mounted to the sleeve; and
   wherein the sleeve is axially contractible relative to the support rod to vary an angle of the vane relative to the support rod.

7. The intravascular stent according to claim 1, wherein the helix angle is about 16 degrees relative to the longitudinal axis of the tubular member.

8. An intravascular stent comprising:
   an expansible tubular mesh member having a collapsed form to be inserted into a vein and an expanded form to be retained within the vein;
   the mesh member having at least one vane stationarilly attached to an interior thereof and extending helically to induce spiral flow of blood, said at least one vane having a helix angle of between 5 and 16 degrees relative to a longitudinal axis of the mesh member.

9. The stent according to claim 8, wherein the mesh member comprises a plurality of wires that extend helically and cross each other to form junctions.

\* \* \* \* \*

UNITED STATES PATENT AND TRADEMARK OFFICE
CERTIFICATE OF CORRECTION

| | | |
|---|---|---|
| PATENT NO. | : 7,682,673 B2 | Page 1 of 1 |
| APPLICATION NO. | : 10/650217 | |
| DATED | : March 23, 2010 | |
| INVENTOR(S) | : John Graeme Houston et al. | |

It is certified that error appears in the above-identified patent and that said Letters Patent is hereby corrected as shown below:

Title Page,

Under
Foreign Application Priority Data

Item (30) delete "Dec. 28, 1998" and insert --Dec. 29, 1998--

Signed and Sealed this

Seventeenth Day of August, 2010

David J. Kappos
*Director of the United States Patent and Trademark Office*